United States Patent
Jarl et al.

(10) Patent No.: US 7,201,724 B2
(45) Date of Patent: Apr. 10, 2007

(54) STYLET UNIT

(75) Inventors: Per Jarl, Järfälla (SE); Rolf Hill, Järfälla (SE); Bengt-Ake Norén, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 72 days.

(21) Appl. No.: 10/482,347

(22) PCT Filed: Apr. 9, 2002

(86) PCT No.: PCT/SE02/00707

§ 371 (c)(1),
(2), (4) Date: Jul. 16, 2004

(87) PCT Pub. No.: WO03/002197

PCT Pub. Date: Jan. 9, 2003

(65) Prior Publication Data

US 2004/0243209 A1     Dec. 2, 2004

(30) Foreign Application Priority Data

Jun. 29, 2001    (SE) .................................... 0102353

(51) Int. Cl.
*A61B 5/00*    (2006.01)

(52) U.S. Cl. ...................................................... 600/585

(58) Field of Classification Search ................ 600/585, 600/372, 373, 374; 604/264, 280, 282; 607/116, 607/122; 606/194

See application file for complete search history.

(56) References Cited

U.S. PATENT DOCUMENTS

| | | | |
|---|---|---|---|
| 4,209,019 A | | 6/1980 | Dutcher et al. |
| 4,573,470 A | * | 3/1986 | Samson et al. ............ 606/194 |
| 4,646,755 A | | 3/1987 | Kane |
| 5,190,050 A | * | 3/1993 | Nitzsche ..................... 600/585 |
| 5,728,148 A | | 3/1998 | Boström et al. |

* cited by examiner

*Primary Examiner*—Max Hindenburg
*Assistant Examiner*—Fangemonique Smith
(74) *Attorney, Agent, or Firm*—Schiff Hardin LLP

(57) ABSTRACT

A stylet unit has a flexible tubular stylet sleeve, a flexible inner stylet wire inserted into a channel of the stylet sleeve with at a least a portion of the stylet wire and at least a portion of the channel each having a non-circular cross section for preventing rotation of the wire inside the sleeve. The stylet unit has a handle with which the sleeve and the stylet wire are movable relative to each other in a longitudinal direction. The sleeve and the wire are connected at one end thereof to the handle, with the sleeve being rotationally arranged within the handle.

16 Claims, 2 Drawing Sheets

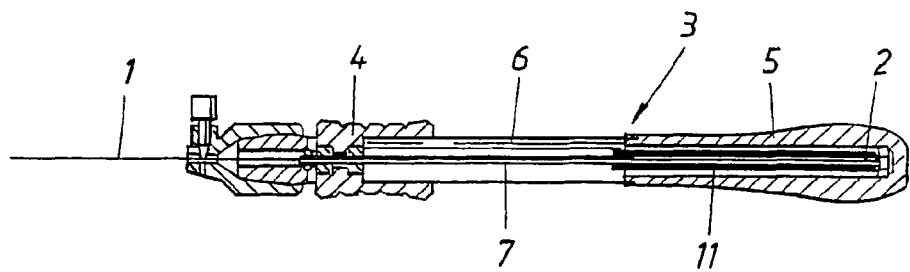
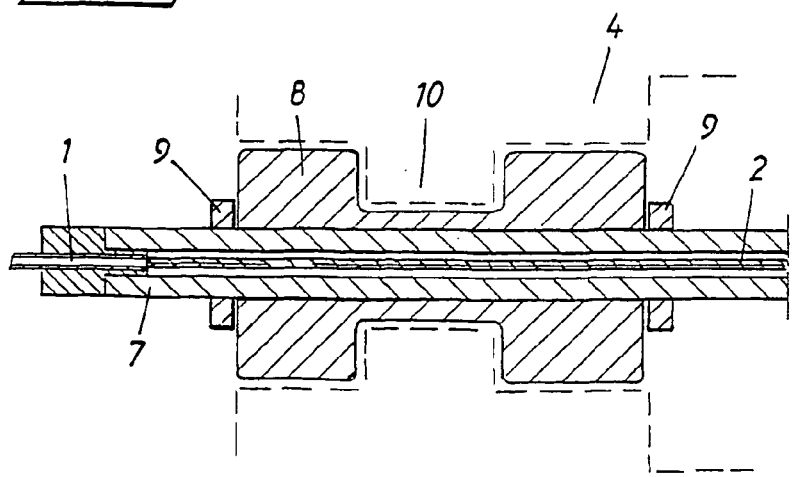

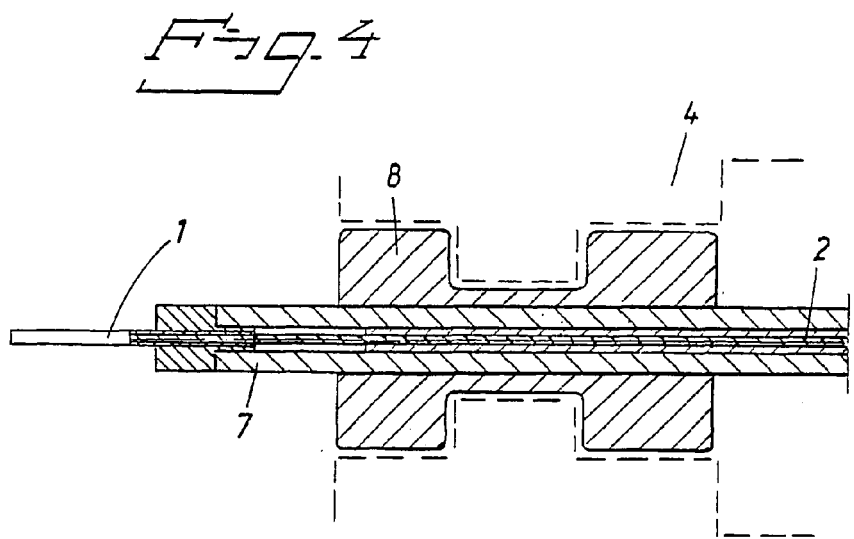
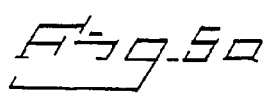 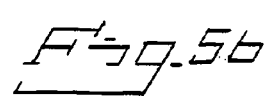 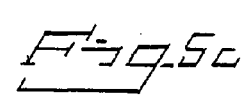
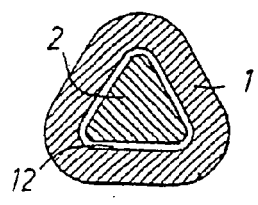 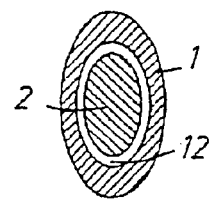 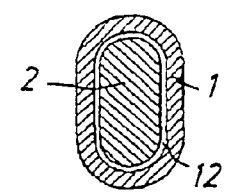
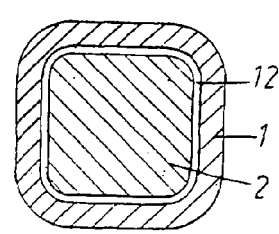 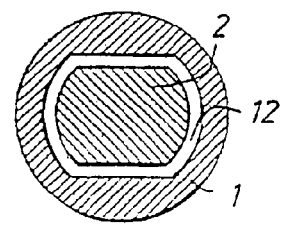

STYLET UNIT

BACKGROUND OF THE INVENTION

1. Field of the Invention

The present invention relates to a stylet unit of the type having a flexible, tubular stylet sleeve, and a flexible inner stylet wire, inserted into the stylet sleeve. At least a portion of the stylet wire and at least a portion of a channel defined by the stylet sleeve has a non-circular cross-section for preventing rotation of the wire inside the sleeve. The stylet unit also has a handle, by means of which the sleeve and the stylet are movable in relation to each other in a longitudinal direction, the sleeve and the wire being connected at one end thereof to the handle.

2. Description of the Prior Art

Stylet units of the above type are widely used for medical purposes. The wire and the sleeve are adapted to be inserted into an oblong element, normally an electrode cable of a heart stimulator that is to be introduced into a mammal body for surgical purposes. The purpose of the unit is to locate the oblong element in the body. Typically, an end of the cable is anchored in the atrium or ventricle of a patient by means of the style unit.

A stylet unit of the above general type is especially suitable for stiffening and maneuvering a hollow electrode cable for a heart stimulator, in conjunction with introduction of the electrode cable into a patient's heart, and for anchoring the contact electrode (electrode head) on the distal end of the cable in a cavity in the heart. Introduction of such an element into the heart is usually performed through a suitable vein, and the contact electrode can be anchored in the right ventricle or atrium. The stylet unit temporarily contained inside the hollow electrode cable extends through the cable's central channel from the cables proximal end (which is subsequently connected to the heart stimulator) to its distal end on which the contact electrode is located.

Especially in the anchoring of a contact electrode in the heart's atrium, a stylet unit is appropriately used with which the distal end section of the electrode cable can be given a suitable shape, simplifying the introduction of the end section into the atrial auricle and anchoring of the contact electrode in the trabeculae of the atrial auricle. After the contact electrode (that is the electrode cable) has been anchored at the desired site in the heart, the stylet unit is withdrawn from the electrode cable.

U.S. Pat. No. 5,728,148 describes and shows a stylet unit with a double stylet combination having a flexible, tubular stylet sleeve holding an inner stylet wire which is moveable in the sleeve's central channel. At the proximal end of this known stylet unit, there is an operating handle with which the sleeve and inner stylet wire can be moved in relation to each other to retract the wire's pre-bent distal end section into the distal end section outside the opening of the sleeve's end section into the central channel of the distal end section of the surrounding electrode cable, thereby imparting the desired bent shape to the end of the cable. Accordingly, a J-shaped distal end of the electrode cable, suitable for anchoring purposes, can be obtained by deploying the distal end section of the pre-bent wire into the electrode channel.

In order to prevent undesirable rotation of the stylet wire in the surrounding sleeve within at least a longitudinal section of the stylet unit, the wire and the sleeve channel having respective corresponding non-circular cross sections along at least a longitudinal section of the stylet. Normally, the non-circular sections are located at the respective distal end of the wire and sleeve. Both the wire and the sleeve are non-rotationally arranged within the handle, in order to permit the maneuvering of the distal end portion of the wire and sleeve.

However, when the handle is turned, for example in order to locate the thus J-shaped (or similarly shaped) and implanted electrode cable end for the exact positioning thereof, the stylet sleeve produces a torsional moment on the end of the wire. This is due to the non-circular sections of the wire and the sleeve still being in engagement with each other in the distal end regions thereof. The torsional moment on the wire might result in the wire being broken or damaged. Therefore, it may occur that a broken end of the wire is left in the electrode cable. Such a broken end may cause a major failure on the implantable lead system, with a detrimental result for the patient.

SUMMARY OF THE INVENTION

An object of the invention is to provide a stylet unit of the type initially described in which any torsional moment applied to the stylet wire due to the turning of the handle does not cause damage or breakage on the wire.

Accordingly, it is an object of the invention to provide a stylet unit that can be turned one or more turns without the risk of thereby damaging the stylet wire due to any torsional moment thereby being applied to the wire via the surrounding sleeve.

It is a further object of the invention to prevent a pre-bent stylet wire from being subjected to a damaging torsional moment from the surrounding stylet sleeve while being in a deployed state inside a human being into which an oblong element is located by means of the stylet unit.

These objects are achieved in accordance with the invention by a stylet unit of the type initially described, wherein the sleeve is rotationally arranged within the handle. When the handle is turned, the sleeve will be free to rotate inside the handle. Accordingly, the sleeve is in an engagement with the handle that permits the operation of the sleeve in a longitudinal direction but leaves the sleeve free to rotate inside the handle. The term "rotationally", as used herein, means rotation around the longitudinal axis of the sleeve.

The stylet wire is non-rotationally fixed to at least a part of the handle. This will be an essential pre-condition for making it possible to maneuver the stylet distal end by turning at least the part of the handle.

Preferably, the handle has a handling element in engagement with the stylet sleeve and movable in a longitudinal direction in relation to the stylet wire, the stylet sleeve being rotationally arranged in relation to the handling element. Thereby, the handling element itself need not be rotationally arranged in relation to the rest of the handle in order to achieve the rotational arrangement of the sleeve.

According to a preferred embodiment the stylet sleeve is fastened to a rigid tube, which is in engagement with the handling element, this tube being rotationally arranged in relation to the handling element. The arrangement of the tube is advantageous from several points of view. Above all it forms a reasonably large body in relation to which the handling element may be rotationally arranged. It would be difficult to position the thin and flexible sleeve directly in a reliable rotational engagement with the surrounding handling element. It should be understood that the word "tube" as used herein does not imply that the tube must have any specific length in the longitudinal direction. Its main purpose is to act as a securing point for the sleeve. However, it may also act as a cover for the wire in case the wire runs through the tube to the part of the handle to which it is secured.

Preferably, the tube has at least one recess for engagement with a corresponding projection of the handling element (or of any intermediate element between the handling element and the tube). Alternatively, or as a complement, the tube has at least one projection for engagement with a corresponding recess of the handling element (or of any intermediate element between the handling element and the tube).

According to the invention, a portion of the wire is pre-bent, this portion being located at an end thereof opposite to the end thereof fastened to the handle. That is, the distal end of the wire is pre-bent. The distal end of the sleeve should be pre-bent in an opposite direction in order to guarantee the straightness of the distal end of the stylet unit when the wire is in a retracted state in the sleeve. The wire and the sleeve channel preferably present non-circular cross sections at their distal ends.

The wire and the sleeve are adapted to be inserted into an oblong element that is to be introduced into a mammal body for surgical purposes, in order to locate the oblong element in the body. The oblong element may be an electrode cable for a heart stimulator, a coronary catheter or any other kind of hollow, oblong instrument.

BRIEF DESCRIPTION OF THE DRAWINGS

FIG. 1 is a schematic cross-sectional view of a part of a stylet unit according to the invention.

FIG. 2 is a schematic cross-sectional view of a detail of the stylet unit shown in FIG. 1.

FIG. 3 is a cross sectional view of the detail shown in FIG. 2 in an enlarged scale.

FIG. 4 is a cross sectional view of an alternative embodiment of the detail shown in FIG. 3.

FIGS. 5a–5e are views showing different cross sections of a section of non-circular stylet wire and stylet sleeve

DESCRIPTION OF THE PREFERRED EMBODIMENTS

FIG. 1 shows a first embodiment of the inventive stylet unit. The stylet unit is especially suitable for stiffening and maneuvering a hollow electrode cable for a heart stimulator (not shown), in conjunction with introduction of the electrode cable into a patient's heart, and for anchoring the contact electrode (electrode head) on the distal end of the cable in a cavity in the heart. Introduction of such an element into the heart is usually performed through a suitable vein, and the contact electrode can be anchored in the right ventricle or atrium. The stylet unit temporarily contained inside the hollow electrode cable extends through the cable's central channel from the cables proximal end (which is subsequently connected to the heart stimulator) to its distal end on which the contact electrode is located.

The stylet unit has a flexible, tubular stylet sleeve 1, and a flexible inner stylet wire 2, inserted into the stylet sleeve 1 and arranged to move freely in a longitudinal direction inside the sleeve 1. Both the sleeve 1 and the wire 2 is preferably are made of a metal such as steel. The sleeve 1 and the wire 2 have a proximal end and a distal end. In the area preceding its distal end, the inner stylet wire 2 has a pre-bent distal end section. Preferably, the sleeve 1 has a corresponding pre-bent distal end section. The sleeve 1 and the wire 2 are pre-bent in opposite directions and the pre-tensioning forces thereof act in the same plane and are adapted such that the pre-bends of the sleeve 1 and the wire 2 cancel each other when the wire 2 is retracted into the sleeve 1. This requires the wire 2 to be kept from rotating in the sleeve 1.

The sleeve 1 and inner stylet wire 2 can be moved in relation to each other to retract the wire's 2 pre-bent distal end section into the distal end section of the surrounding sleeve 1, or to deploy the pre-bent distal end section outside the opening of the sleeve's 1 end section into the central channel of the distal end section of the surrounding electrode cable, thereby imparting the desired bent shape to the end of the cable. Accordingly, a J-shaped distal end of the electrode cable, suitable for anchoring purposes, can be obtained by deploying the distal end section of the pre-bent wire 2 into the electrode channel. Sleeve 1 and wire 2 are introduced into the electrode cable, or similar oblong element to be implanted, in order to stiffen the latter and enable it to be guided through and be located in the patient. After the location having been completed the stylet unit is retracted out of the electrode or the like via the proximal end thereof.

Each of at least a portion of the stylet wire 2 and at least a portion of a channel defined by the stylet sleeve 1 has a non-circular cross-section for preventing undesirable rotation of the wire 2 inside the sleeve 1. Examples of non-circular cross section of the sleeve 1 and the wire 2 are shown in detail in FIGS. 5a–5e. The non-circular sections of the wire 2 and the sleeve 1 are preferably located at or near the distal ends thereof, and have lengths of approximately 5–10 cm. However, other positions and lengths of interacting, non-circular cross sections of the wire 2 and the sleeve 1 are possible.

The stylet unit also has a handle 3, by means of which the sleeve 1 and the stylet wire 2 are movable in relation to each other in a longitudinal direction, the sleeve 1 and the wire 2 being connected at one end thereof, the proximal end, to the handle 3.

The handle 3 has a handling element 4, a handle part 5 and a guide element 6 along which the handling element 4 is movable towards and from said part 5 of the handle. Handling element 4, handle part 5 and guide element 6 preferably are made of a polymer material.

The handling element 4 is generally ring-shaped and has a channel or central opening through which the wire 2 extends to the handle part 5. It also has guiding recesses via which it is in engagement with the guide element 6. The handling element 4 is non-rotationally arranged in relation to the guide element 6. It is intended that the handling element 4 be gripped outwardly by an operator for the moving thereof in relation to the handle part 5 and guide element 6.

The handling element 4 is indirectly connected to the sleeve 1 by a tube 7 and an intermediate element 8 and is used for moving the sleeve 1 in a longitudinal direction in relation to the wire 2. The sleeve 1 is fastened to the tube 7. The tube 7, preferably made of a metal such as steel, is rotationally arranged in relation to the handling element 4. By manually moving the handling element 4 toward the handle part 5, to which the wire is connected, the distal end of the wire 2 is deployed from the distal end of the sleeve 1.

The intermediate element 8 comprises a bracket, for example ring-shaped with an inner diameter corresponding to the outer diameter of the tube 7. According to a first embodiment, shown in FIG. 3, the intermediate element 8 is rotationally arranged in relation to the tube 7. Preferably it is made of metal or the same material as the tube 7. On the tube 7 there are provided projections 9 on each side of the intermediate element 8, in engagement with and locking the intermediate element in the longitudinal direction in relation to the tube 7. The projections 9 could be any projection attached to the tube 7 either as an integrated part of the tube 7 or as a separate part, such as a cylindrical ring, attached to the tube 7 by means of welding, brazing, gluing etc. The outer periphery of the intermediate element 8 has a recess 10 into which a corresponding projection of the handling element 4 is to be inserted. The recess 10 is, but need not be, adapted to permit rotation of the handling element 4 in relation to the intermediate element 8, since rotation between the sleeve 1 and the handling element is provided by the connection between the tube 7 and the intermediate element 8. In other words, the intermediate element 8 need not be rotationally arranged in relation to the handling element 4 for achieving the inventive purpose, but may be so in order to, for example, provide for a rotational relationship even in case the tube 7 would accidentally stick to the intermediate part 8.

As an alternative to the projections 9, the tube could be provided with a recess with which a corresponding projection on the intermediate element 8 could be in engagement in order to provide for the fixing of the tube 7 in relation to the intermediate element 8 in the longitudinal direction of the sleeve 1 and wire 2.

According to a second embodiment, shown in FIG. 4, the intermediate element 8 is non-rotationally arranged in relation to the tube 7. The tube 7 is preferably made of the same material as the intermediate element 8 and could be attached to the later by a weld joint, braze joint, glue joint etc.

It should be emphasized that a number of alternative embodiments will be obvious for a man skilled in the art concerning how to achieve the rotational arrangement of the sleeve in relation to the handling element 4, and that such embodiments are within the scope of the invention. Accordingly, the tube 7 can be any element presenting a through hole for the passage of the wire 2. The intermediate part 8 is preferred, but may as well be omitted as long as there is a provided any engagement means between the handling element 4 and the tube 7. Such engagement means could include stop rings or any other projection arranged on any one of the tube 7 and the handling element 4, inhibiting longitudinal movement of the handling element 4 in relation to the tube 7 but permitting rotation of the tube 7 in relation to the handling element 4. The invention also includes embodiments (not shown) in which the sleeve 1 is rotationally fastened to a tube corresponding to the tube 7 or to a handling element corresponding to the handling element 4. Corresponding engagement means, inhibiting mutual longitudinal movement and permitting mutual rotation, should then be provided on the sleeve 1 and/or the part to which it is fastened.

The handle part 5 may be a separate part or an integrated part of the guide element 6. Here, the handle part 5 is fastened to the guide element 6 by means of a thread joint at the end of the guide element 6. For this purpose the handle part 5 has a recess having an inner threading (not shown in detail). This means that at least temporarily, during use of the stylet unit, the handle part 5 of the handle 3 is non-rotationally arranged in relation to the guide element 6 and in relation to the handling element 4. The proximal end of the wire 2 is fastened to the bottom of the handle part 5. Preferably, a tube 11, preferably made of metal, for covering and guiding the wire 2 is fastened to or integrated with the handle part 5. For this purpose the inner diameter of the tube 11 is only slightly larger than the diameter of the wire 2. The tube 7 to which the sleeve 1 is fastened is telescopically arranged in relation to the cover and guide tube 11 such that the first tube 7 is inserted into the latter tube 11 when the handling element 4 is moved toward the handle part 5. The length of each tube 7, 11 is adapted such that they overlap each other in all positions of the handling element 4 in relation to the handle part 5. Thereby, the proximal end part of the wire 2 not covered by the sleeve is constantly covered by the tubes 7, 11.

It is intended that the handle part 5 be gripped by an operator and that, by rotating it, the position of the distal end of the wire 2 inside the patient can be adjusted. The rotational arrangement of the sleeve 1 in the handle 3 prevents the sleeve from implying unwanted torsional moment on the wire 2 upon turning or rotation of the handle 3 while the distal end of the wire 2 is deployed from the distal end of the sleeve 1.

FIGS. 5a–5e show different types of non-circular cross-sections of the sleeve 1 and the wire 2. The gap or spacing 12 between the outer periphery of the wire 2 and the inner periphery of the sleeve 1 is adapted to enable smooth mutual movement in the longitudinal direction but small enough to prevent rotation of the wire 2 inside the sleeve 1.

Although modifications and changes may be suggested by those skilled in the art, it is the invention of the inventors to embody within the patent warranted heron all changes and modifications as reasonably and properly come within the scope of their contribution to the art.

The invention claimed is:

1. A stylet unit comprising:
    a flexible, tubular stylet sleeve defining a channel therein;
    a flexible inner stylet wire disposed in said channel of said stylet sleeve, at least a portion of said stylet wire and at least a portion of said channel each having a non-circular cross section for preventing rotation of said wire inside said sleeve;
    a handle connected to one end of said sleeve and one end of said wire for moving said sleeve and said wire relative to each other in a longitudinal direction; and
    said sleeve being rotationally arranged within said handle to allow rotation of said handle relative to said sleeve.

2. A stylet unit as claimed in claim 1 wherein said stylet wire is non-rotationally fixed to at least a part of said handle.

3. A stylet unit as claimed in claim 1 wherein said handle comprises a handling element engaging said stylet sleeve and movable in a longitudinal direction relative to said stylet wire, said stylet sleeve being rotatable relative to said handling element.

4. A stylet unit as claimed in claim 3 comprising a rigid tube fastened to said stylet sleeve, said rigid tube engaging said handling element and being rotatable relative to said handling element.

5. A stylet unit as claimed in claim 4 wherein said tube has a recess and wherein said handling element has a projection engaging said recess.

6. A stylet unit as claimed in claim 4 wherein said handling element has a recess and wherein said tube has a projection engaging said recess.

7. A stylet unit as claimed in claim 4 comprising an intermediate element disposed between said handling element and said tube and engaging said tube and said handling element, said intermediate element being rotatable relative to at least one of said handling element and said tube.

8. A stylet unit as claimed in claim 7 wherein said intermediate element has a recess and wherein said handling element has a projection engaging said recess.

9. A stylet unit as claimed in claim 7 wherein said handling element has a recess and wherein said intermediate element has a projection engaging said recess.

10. A stylet unit as claimed in claim 7 wherein said intermediate element is a bracket that is rotationally arranged around said tube and non-rotationally arranged relative to said handling element.

11. A stylet unit as claimed in claim 3 wherein said stylet wire is non-rotationally fixed to at least a part of said handle, and comprising a guide element along which said handling element is movable toward and from said part of said handle.

12. A stylet unit as claimed in claim 11 wherein said handling element is non-rotationally arranged relative to said guide element.

13. A stylet unit as claimed in claim 11 wherein, at least temporarily during use of said stylet unit, said part of said handle is non-rotationally arranged relative to said guide element and relative to said handling element.

14. A stylet unit as claimed in claim 1 wherein each of the non-circular portion of the channel of the sleeve and the non-circular portion of the wire are disposed at respective ends of the sleeve and the wire opposite to respective ends of the sleeve and the wire fastened to the handle.

15. stylet unit as claimed in claim 1 wherein said wire has a pre-bent portion, said pre-bent portion being disposed at an end of said wire opposite to an end of the wire fastened to the handle.

16. stylet unit as claimed in claim 1 comprising an oblong element adapted to receive said wire and said sleeve therein, said oblong element being adapted for introduction into a living body for medical purposes.

* * * * *